United States Patent [19]
Hakala

[11] Patent Number: 5,873,361
[45] Date of Patent: Feb. 23, 1999

[54] METHOD OF PREVENTING THE FORMATION OF A DANGEROUS UNDERPRESSURE IN A RESPIRATORY SYSTEM

[75] Inventor: Matti Hakala, Helsinki, Finland

[73] Assignee: Instrumentarium Corp., Helsinki, Finland

[21] Appl. No.: 559,474

[22] Filed: Nov. 15, 1995

[30] Foreign Application Priority Data

Nov. 14, 1994 [FI] Finland ..................................... 945369

[51] Int. Cl.⁶ .................................................. A61M 16/00
[52] U.S. Cl. ............................. 128/204.23; 128/204.22; 600/529
[58] Field of Search ........................ 128/204.23, 204.22, 128/204.21, 204.26; 600/529, 532

[56] References Cited

U.S. PATENT DOCUMENTS

| | | | |
|---|---|---|---|
| 3,741,208 | 6/1973 | Jonsson et al. ..................... | 128/204.21 |
| 4,413,632 | 11/1983 | Schlessinger et al. ................... | 128/716 |
| 4,565,194 | 1/1986 | Weerda et al. ...................... | 128/204.23 |
| 5,050,615 | 9/1991 | Malkamaki .............................. | 128/719 |
| 5,111,827 | 5/1992 | Rantala ................................. | 128/719 |
| 5,394,881 | 3/1995 | Block, Jr. ................................. | 128/716 |

FOREIGN PATENT DOCUMENTS

| | | |
|---|---|---|
| 829409 | 3/1960 | United Kingdom . |
| 90/14043 | 11/1990 | WIPO ............................ A61B 5/087 |

*Primary Examiner*—John G. Weiss
*Assistant Examiner*—V. Srivastava
*Attorney, Agent, or Firm*—Andrus, Sceales, Starke & Sawall

[57] ABSTRACT

A method of preventing the formation of dangerous underpressure in a respiratory system,, which comprises a respirator (1) connected to the patient, and a sampling device (11) and a gas analyzer (3) connected thereto, in which method inspired and expired air is aspirated at a predetermined pressure for sampling through the sampling line (7). When an excess underpressure is formed in the gas analyzing unit, the aspiration of the pump (2) is prevented in the respiratory tube (15).

17 Claims, 4 Drawing Sheets

METHOD OF PREVENTING THE FORMATION OF A DANGEROUS UNDERPRESSURE IN A RESPIRATORY SYSTEM

BACKGROUND OF THE INVENTION

The object of the invention is a method of preventing the formation of dangerous underpressure in a respiratory system.

When the patient is connected to a respirator, a pressure generally prevails which is at least the same as the ambient pressure. During inspiration an overpressure is required to fill the patient's lungs, and the pressure decrease is often even restricted in the expiration phase in order to prevent the collapsing of the patient's lungs, for which is used the term PEEP, Positive End-Expiratory Pressure. The occurrence of underpressure, on the other hand, is exceptional in such a system and is generally considered as injurious. At the worst underpressure can cause absorption of fluid from the tissue to the lungs and lead to permanent injuries. The allowed underpressure is only some centimeters of water.

In connection with respiratory breathing it is nowadays customary to measure the concentrations of gases inspired and expired, especially the carbon dioxide, oxygen and anesthetic gas concentrations. This is generally made by aspirating a small amount of gas, typically about 200 ml/min into a monitor that analyzes the concentrations of the desired gases and displays the result on e.g. a display.

The amount of sample gas taken by the gas monitor is in normal conditions insignificant compared to the respiratory gas amount fed into the system, the so called fresh gas flow, which generally is several liters per minute. Even in extreme cases, when the fresh gas flow is below 1 l/min., when a so called low flow anesthesia is involved, the gas amount discharged from the system can easily be substituted by increasing the fresh gas flow correspondingly.

There are, however, cases when due to human error or equipment failure the gas feed into the system has been interrupted. The gas amount aspirated by the monitor is in such cases not substituted at all, but the monitor aspirates into the respiratory system a growing underpressure, which is limited only by the capability of the pump to generate underpressure, and on the other hand by a possible leakage in the system, which again in itself is not a desired property. The underpressure can, dependent on the gas volume of the system, fairly quickly reach a limit where the patient's safety for the above reasons is jeopardized.

There has been no previous method available to secure the prevention of such an underpressure formation. The gas monitors generally measure the pressure of their own internal sampling system, which in principle is also dependent on the pressure of the patient system. The dependence is, however, not unambiguous, as the difference between these pressures also depends e.g. on the flow resistance in the sampling line. A sudden pressure decrease is generally caused by constriction in the sampling line, wherefore it cannot reliably be used to indicate the pressure prevailing in the patient tube system.

New respirators have usually a built-in airway pressure monitoring, some also provided to alarm when the pressure falls below a preset limit. There are, however, quite many old devices in use which lack these properties. Moreover, it is quite possible that despite monitoring and alarm, the locating of the problem and the repair of the failure take so long that the patient will already suffer from the situation. The ventilator patient tube might also constrict, thus putting the ventilator safety equipment out of function. No means have been provided so far to prevent the occurrence of such a situation.

SUMMARY OF THE INVENTION

The method according to the invention provides a decisive improvement of the above mentioned disadvantages. The invention is characterized in what is presented in the claims.

The invention provides a considerable improvement of the safety of a patient connected to a respirator. The invention provides preferably separately an error message about a constriction in the sampling line as well as of underpressure in the respiratory tube. The patient circuit underpressure can be identified by the invention to differ from a constriction in the sampling line. The underpressure error message can quickly be located with the subject invention.

BRIEF DESCRIPTION OF THE DRAWINGS

The invention is below presented with reference to the enclosed drawing, in which.

DETAILED DESCRIPTION OF THE PREFERRED EMBODIMENT

Figure 1:
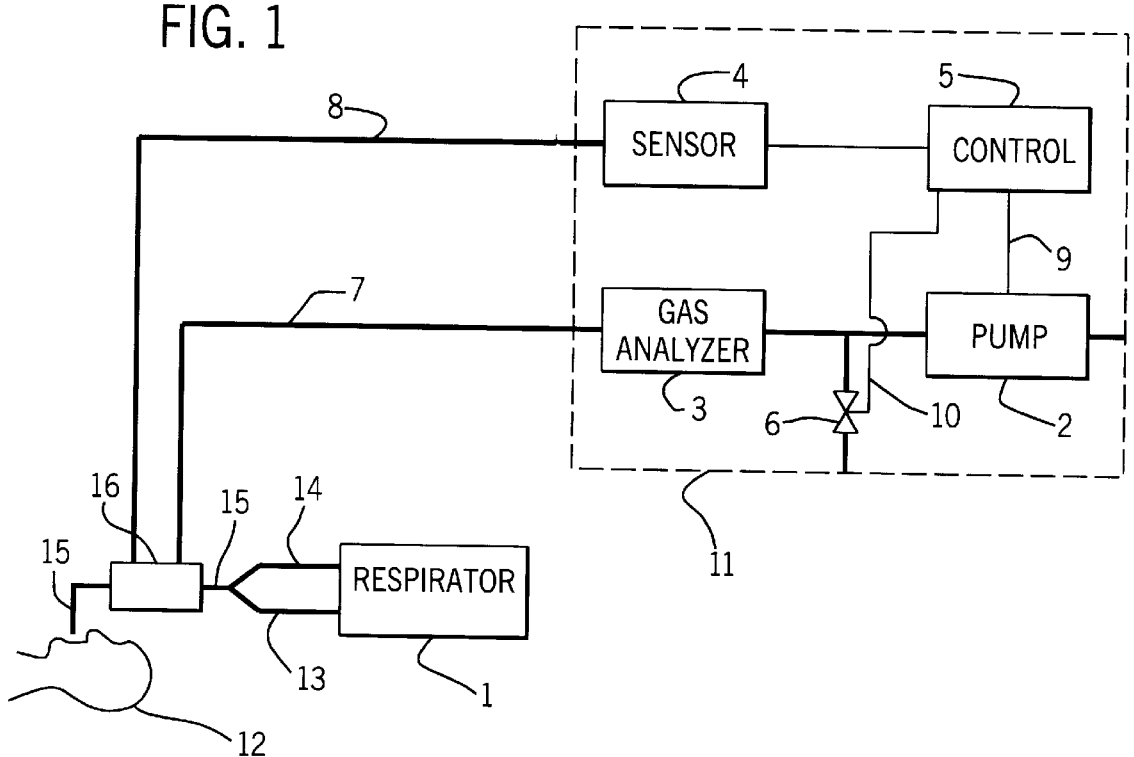
FIG. 1 presents a basic view of a respirator and a gas measuring device.

FIG. 1 presents one favorable embodiment of the invention, in which a patient 12 is connected to a respirator 1 The respirator comprises an inspiration tube 13, which carries inspiration air or oxygen to the patient, and an expiration tube 14, which returns the expiration gases from the patient back to the respirator. The tubes 13, 14 are, close to the patient, connected into one tube 15, which as such or through an adapter attached thereto can be connected to an intubation tube, which through the patient's mouth or nose can be led to the trachea or to the mask. To this combined tube 15, or to the adapter 16 attached thereto, has then been connected a sampling line 7, through which are aspirated samples of the patient's respiratory gas, which can be the inspiration and/or the expiration gas. The cross-sectional area of the opening provided for the sampling in the adapter 16 or in the tube 15, or of the sampling line 7 extending from the opening is generally smaller than the cross-sectional area of the tube 15. The sample is preferably aspirated through the sampling line by the pump 2 of the monitor 11 to the gas analyzing unit 3, in which the patient's inspired and/or expired gas is analyzed. The analyzing can comprise the measuring or identifying, or both, of one or several gas component concentrations. Carbon dioxide, oxygen and anesthetic gases are generally analyzed.

A second line 8 for measuring the pressure is preferably connected to the tube 15 or to the adapter 16 attached thereto. A member 4 observing the underpressure and generally called the pressure sensor, is attached to the pressure measuring line 8 to measure the pressure caused by the gas in the respiratory tube system. The pressure measuring can be carried out by comparing the pressure prevailing in the respiratory tube 15 with the pressure outside the tube, i.e. the ambient pressure. The gas sampling pump 2 is controlled through the signal way 9 from the control unit 5, which receives information about the pressure variation. According to the invention, when the information about the gas pressure is below a certain predetermined pressure, the sampling from the respiratory tube 15 connected to the patient is prevented. This can be realized e.g. by stopping the pump. The control unit can simultaneously send a signal through the connection 10 to the valve 6, through which there is a connection to the ambient air, to open the valve to prevent the underpressure possibly formed in the tubes from injuring the patient. The pressure of the lines 7 and 8 is then the same as the ambient pressure, and the disadvantages caused by the aspiration can be eliminated.

The pressure measuring could as well take place locally in the tube 15 or in the adapter 16, whereby the line 8 would not be needed. The tube could then be replaced by a wire to transfer the signal to the control unit 5.

Figure 2:
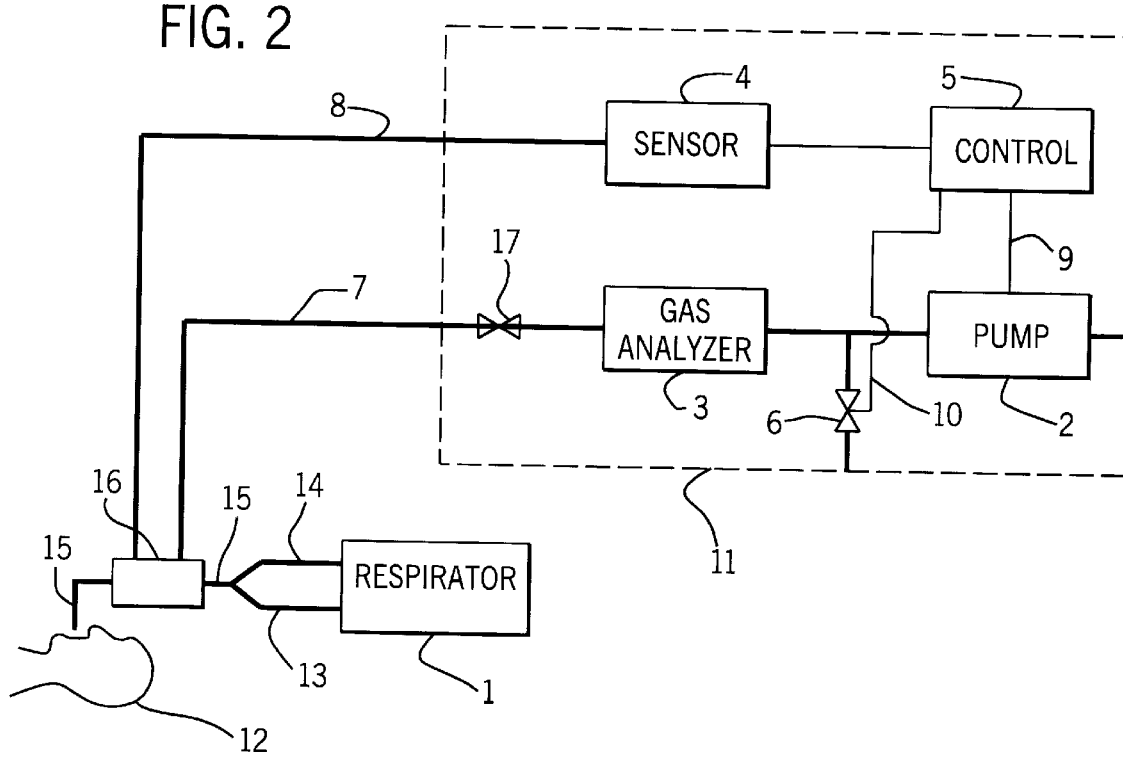
FIG. 2 presents an alternative of the solution of FIG. 1, FIG. 3A and B show different connections of the sampling line to the respiratory tube or to the adapter.

There are also other means available than the ones presented above to prevent the formation of underpressure injurious to the patient. The pump could remain in function, but when the gas pressure falls below the predetermined value, the aspiration from the respiratory tube 15 would be prevented by a valve 17 provided between the pump and the respiratory tube. This valve could simply be an open-closed valve according to FIG. 2. The flow connection between the patient and the pump is then closed. It would further be sufficient to prevent the formation of underpressure by turning the valve 6 into open position to enable the ambient gas to flow through this valve 6 into the line 7. A sufficient flow through the valve 6 would make the stopping of the pump almost unnecessary. Another alternative solution could be based on the valve 17 located in the line 7 between the pump and the respiratory tube, which valve when aspirating the sample could be in a position where the pump aspiration would be connected to the respiratory tube, but due to the formed dangerous underpressure in the respiratory tube, the valve 17 would he connected to aspirate the ambient gas, thus interrupting the aspiration from the respiratory tube.

A favorable device for the embodiment of the method according to the invention has been presented above, in which device an airway pressure measuring by means of a pressure sensor 4 has been connected to a gas monitor. Due to this the device has constantly current information about the pressure prevailing in the respiratory tube system and thereby also in the airway. The gas sampling pump can be controlled with the information provided by the pressure sensor. The valve 6, in one favorable embodiment of the invention, can be used when desired, as often is the case, to aspirate room air to the device instead of sampling gas from the patient for the calibration of the measuring.

The concentrations of carbon dioxide, oxygen, nitrous oxide and anesthetic agents can, when necessary, be measured or identified in the gas measuring unit, The measuring units are in connection with a microprocessor enabling the generating of the alarms and/or the collecting of data. Before the gas reaches the measuring unit, water is separated from the gas into a water trap, the construction and function of which have been described in e.g. the U.S. Pat. Nos. 4,304,578, 4,382,806 and 4,886,528. In the water trap, the sample flow can be divided into two parts, a flow to be analyzed and a side-flow. The flow quantity to the analyzing devices is usually controlled by a throttle. The gas pressure and flow measuring analytics, when a separate pressure measuring line is in question, is also in connection with the control unit microprocessor, from which there is, according to the invention, a connection to the pump to control the pump so that underpressure is not generated in the respiratory tubes because of the pump. A key-board is normally attached to the processor for the feeding of the necessary information, as well as a display and necessary loudspeakers for the alarms to inform about e.g. values above and below defined limit-values.

Figure 3A:
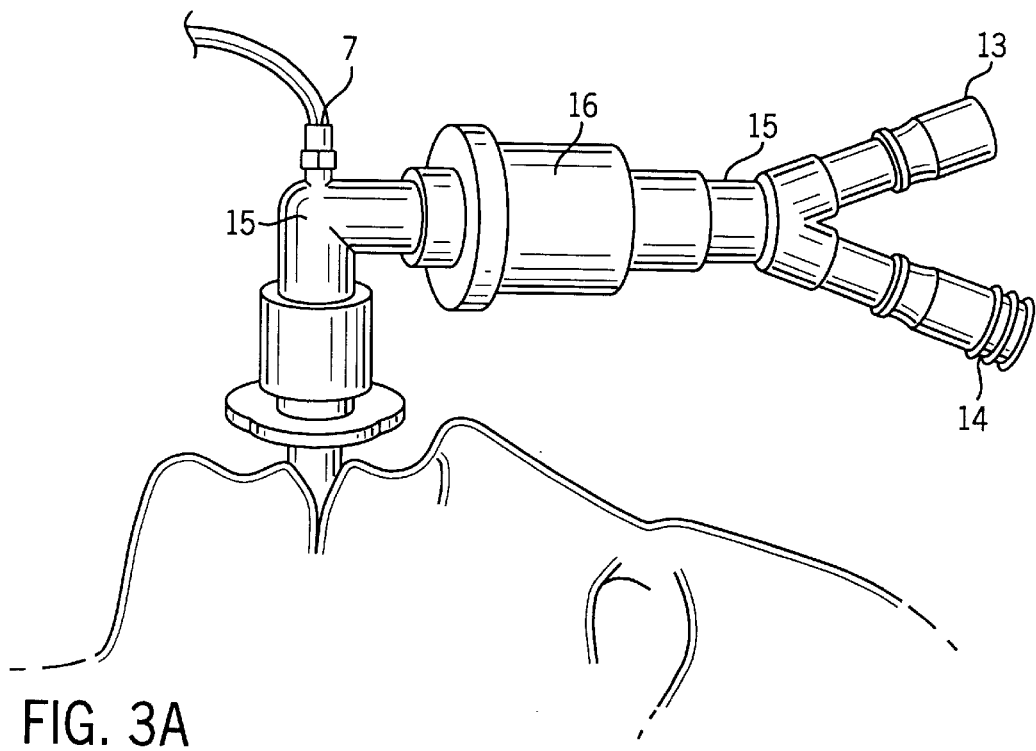

FIGS. 3A and B present different possibilities of connecting the sampling lines to the respiratory tubes, when either one or several tubes are used. FIG. 3A shows a respiratory tube 15 connected to the patient and the respiratory tubes 13 and 14 with an adapter 16 in between. A sampling line 7 is provided in the adapter 16 opening. FIG. 3A shows a typical endotracheal intubation. A tracheostomy tube or a mask ventilation system can also be used as well as paediatric respiratory systems.

Figure 3B:
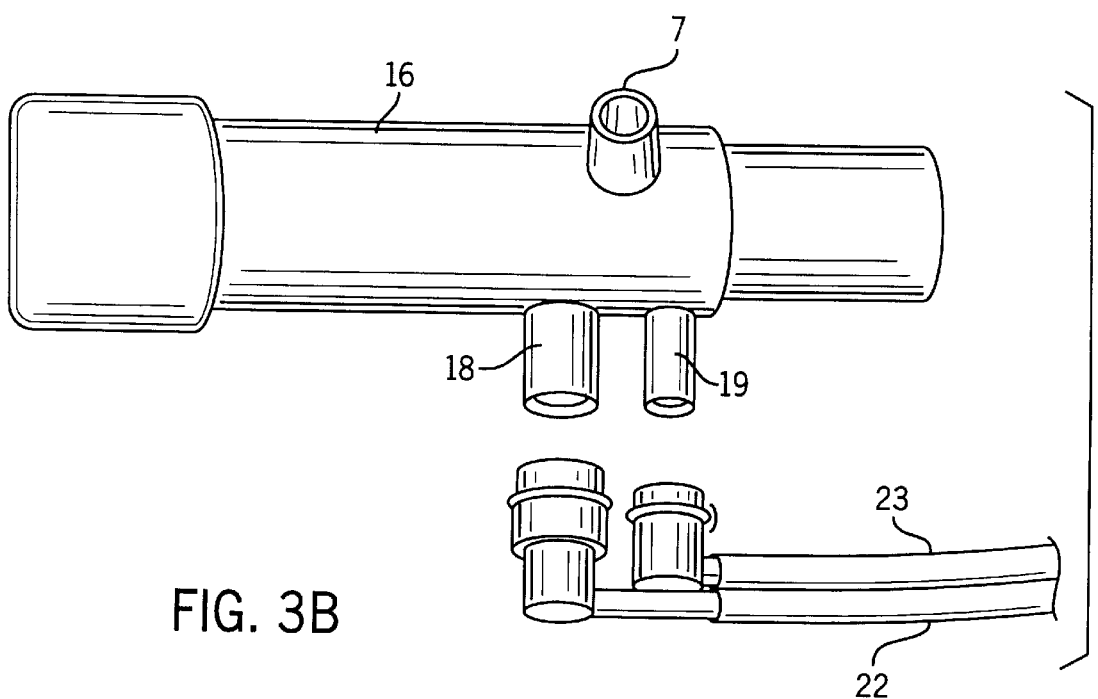

FIG. 3B presents one favorable adapter alternative 16 to be connected to the respiratory tube 15. This is a flow sensor, the construction and function of which have more specifically been described in the U.S. Pat. Nos. 5,111,827, depicted in FIG. 4, and 5,088,332. The flow measuring thus takes place by measuring the pressure difference over the throttle 20. For this purpose, the side of the adapter is provided with two openings 18, 19, through which the pressure signal received from the different sides of the throttle 20 is led through the line 8 to the pressure difference observing member 21. The line 8 has then two channels 22, 23. Either one of these channels can further be connected to the pressure sensor 25, which thus compares the pressure in the respiratory tube with the ambient pressure. A connection is provided between the channels 22, 23, which can be controlled by a magnetic valve 24. The member 21 observing the pressure difference prevailing in the tube 15 over the throttle 20 can also be used instead of the sensor 25 to observe the underpressure in the respiratory tube, because the pressure difference over the throttle deviates considerably from normal condition due to the dangerous underpressure generated in the respiratory tube. The signal received from the pressure difference observing member 21 can be transmitted to the control unit, because the pressure difference observing member 21 is connected with a wire to the control unit 5. A sampling line 7 is connected to the third opening in the adapter for the aspiration of the sample to the analyzing unit. An appropriate technique is naturally required to generate the signal and to transmit it to the control unit. The adapter shown in FIG. 4 can be used to measure the pressure either by measuring the flow magnitude or the pressure difference, or both can be used together. The flow measuring can e.g. compare the behavior of the flow as a function of time.

The adapter can e.g. be used for common endotracheal intubation. The adapter in FIG. 3B is known by the Instrumentarium Oy's brand name D-LITE™ or PEDE-LITE™.

A dangerous underpressure is generally in the magnitude of $-20$ cmH$_2$O, but already e.g. an underpressure value of $-5$ cmH$_2$O can cause emergencies, if the effect of the underpressure is for more than one minute. The ambient pressure of the tubes is generally the 0-level, which is the atmospheric pressure, i.e. approx. 1 atm. The expiration pressure is generally the same as the ambient pressure and at inspiration smaller than 30 cmH$_2$O.

The flow can alternatively be measured so that, knowing that the expiration and inspiration flows follow predetermined curves, a sudden change in the flow depicting curve in relation to comparative curves could cause an alarm of underpressure in the respiratory tube. The underpressure thus generates an error and alarm message.

Different alternatives are possible. The adapter 16 provided in the respiratory tube 15 can be according to FIG. 4, with which is measured either the pressure or the flow magnitude or both together. The adapter 16 can be attached from its one end either to the intubation tube or directly to the mask or to endotracheal intubation, which are not separately shown in the pictures. Different connectors might be required or a respiratory tube as in the FIGS. 1 and 2.

Figure 4:
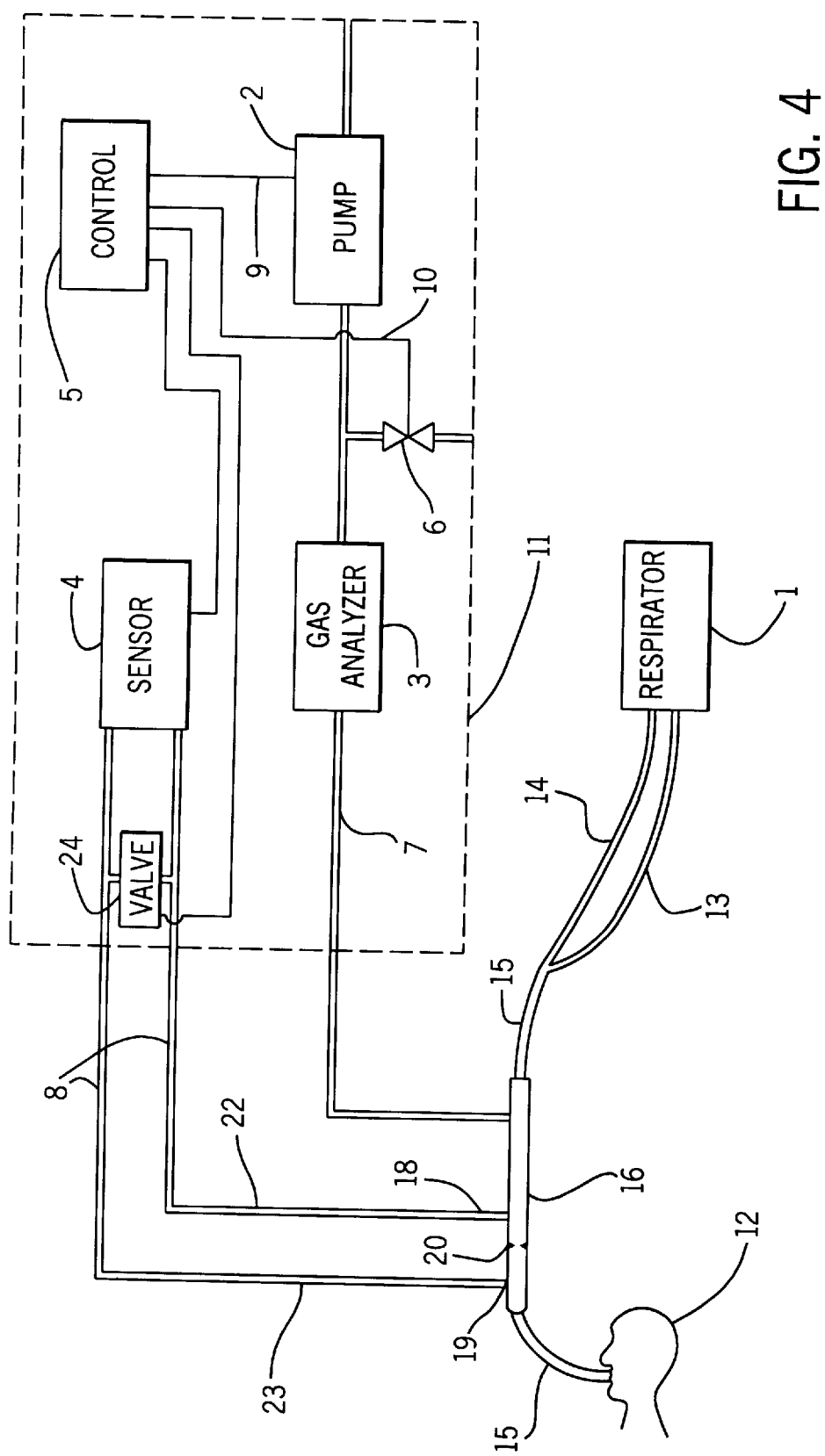
FIG. 4 presents gas measuring options to be connected to the respiratory tube.
Figure 5:
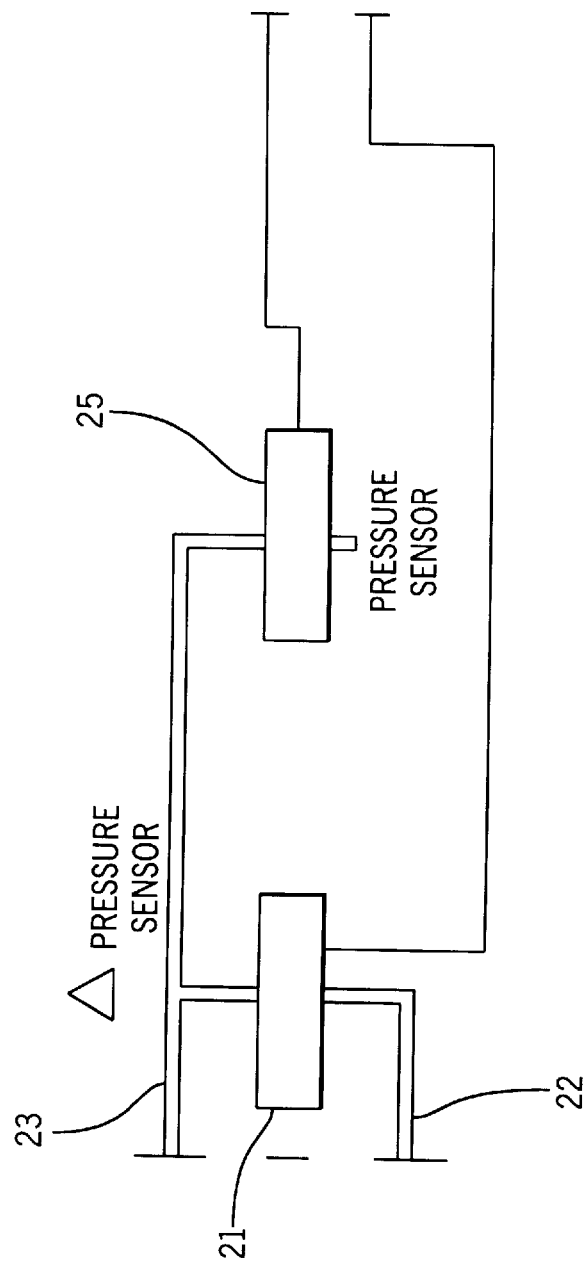
FIG. 5 shows a more detailed view of the underpressure indicating device of FIG. 4.

FIG. 5 presents a partial view of FIG. 4. The underpressure observing member 4 can be a pressure or flow measuring device, e.g. the device 21, which measures the flow by observing the pressure difference over the throttle 20 provided in the adapter 16, and a sensor 25 comparing the tube pressure with the ambient air. Both can be used together for the measuring or only one of them.

The invention has above been described with reference to only one of its embodiments. The invention is not to be considered as so restricted, but all modifications and alternatives, e.g. in the flow measuring, are possible within the scope of the inventive idea according to the claims below.

I claim:

1. In a respiratory system supplying and removing breathing gases to and from a patient through a respiratory conduit, in which system, pressure exists in the respiratory conduit, and in which system, gas samples are aspirated from the system, a method for preventing the occurrence of pressure less than a desired minimum pressure in the system resulting from the aspiration of gas samples from the system, the method thereby preventing resulting injury to a patient, the method comprising the steps of:

sensing a property of the breathing gases indicative of the pressure existing in the respiratory conduit;

comparing the sensed property with a datum indicative of the minimum pressure desired in the system; and terminating the aspiration of gas samples from the system when the sensed property indicates the pressure existing in the conduit is less than the desired minimum pressure.

2. A method according to claim 1 wherein the breathing gases exhibit gas pressure properties and gas flow properties in the respiratory conduit and wherein the sensing step is further defined as sensing one of breathing gas pressure properties or breathing gas flow properties in the conduit.

3. A method according to claim 1 wherein the respiratory system exists in an ambient environment having an ambient pressure and wherein the sensing step, is further defined as sensing the pressure existing in the conduit and the comparison step is further defined as comparing the sensed pressure with a datum comprising the ambient pressure.

4. A method according to claim 3 wherein the respiratory system includes a control unit, said method further including the step of providing the results of the comparison to the control unit for terminating the aspiration of gas samples from the system when the sensed pressure is less than the ambient pressure.

5. The method according to claim 1 wherein a throttle is provided in the respiratory conduit of the respiratory system, and wherein the sensed property is a pressure difference obtained from a flow of the breathable gases over the throttle provided in the conduit.

6. The method according to claim 5 wherein the throttle has an upstream side and a downstream side with respect to the flow of breathable gases in the conduit and wherein the pressure difference is obtained by sensing the pressure on both sides of the throttle.

7. The method according to claim 6 wherein the respiratory system includes a control unit, said method being further defined as including the step of providing the results of the comparison to the control unit for terminating the aspiration of gas samples from the system when the pressure in the conduit is less than the desired minimum pressure.

8. The method according to claim 1 wherein the aspiration of gas samples from the system is carried out by a pump and wherein the terminating step is further defined as stopping the pump when the sensed property indicates the pressure existing in the conduit is less than the desired minimum pressure.

9. The method according to claim 1 wherein the gas samples are aspirated from the system along a sampling flow path connected to the respiratory conduit and containing a pump and wherein the terminating step is further defined as blocking the sampling flow path upstream of the pump in the sampling flow path when the sensed property indicates the pressure existing in the conduit is less than the desired minimum pressure.

10. The method according to claim 1 wherein the respiratory system exists in an ambient environment, wherein the gas samples are aspirated from the system along a sampling flow path connected to the respiratory conduit, wherein the system includes a valve venting the sampling flow path to the ambient environment and wherein the terminating step is further defined as venting the sampling flow path to the ambient environment when the sensed property indicates the pressure in the conduit is less than the desired minimum pressure.

11. The method according to claim 10 wherein the sampling flow path contains a pump for aspirating the gas samples and wherein the terminating step is further defined as stopping the pump when the sensed property indicates the pressure in the conduit is less than the desired minimum pressure.

12. The method according to claim 1 wherein the aspiration of gas samples employs a sampling flow path connected to the respiratory conduit and wherein the breathing gas property sensing is carried out separately from the aspiration of gas samples in the sampling flow path.

13. A method according to claim 12 wherein the aspiration of gas samples employs a sampling flow path connected to the respiratory conduit, wherein the breathing gas property sensing is carried out separately from the aspiration of gas samples in the sampling flow path, and wherein the venting of the sampling flow path to the ambient environment equalizes the pressure in the sampling flow path and respiratory conduit.

14. A method according to claim 10 wherein the sampling flow path includes a gas analyzer, said method further including the step of drawing ambient air into the gas analyzer through the venting valve for calibrating the gas analyzer.

15. The method according to claim 10 wherein the gas sampling flow path includes a gas analyzer downstream of the venting valve and wherein the method is further defined as connecting the gas analyzer in the flow path with the venting valve to analyze the breathing gases and as venting the sampling flow path to the ambient environment with the venting value when the sensed property indicates the pressure in the conduit is less than the desired minimum pressure.

16. In a respiratory system supplying and removing breathing gases to and from a patient through a respiratory conduit, in which system, pressure exists in the respiratory conduit, and in which system, gas samples are aspirated from the system, a method for preventing the occurrence of pressure less than a desired minimum pressure in the system resulting from the aspiration of gas samples from the system, the method thereby preventing resulting injury to a patient, the method comprising the steps of:

sensing the pressure existing in the respiratory conduit;

comparing the sensed pressure with a minimum pressure desired in the system; and terminating the aspiration of gas samples from the system when the sensed pressure is less than the desired minimum pressure.

17. In a respiratory system supplying and removing breathing gases to and from a patient through a respiratory conduit, in which system, pressure exists in a respiratory conduit, and in which system, gas samples are aspirated from the system, a method for preventing the occurrence of pressure less than a desired minimum pressure in the system resulting from the aspiration of gas samples from the system, the method comprising the steps of:

sensing the gas flow properties of the breathing gases passing through the respiratory conduit;

comparing the sensed flow properties with a flow property datum indicative of the minimum pressure desired in the system; and terminating the aspiration of gas samples from the system when the comparison of the sensed flow properties and the flow property datum determines that the pressure in the conduit is less than the desired minimum pressure.

* * * * *